United States Patent
Toya et al.

(10) Patent No.: US 10,492,739 B2
(45) Date of Patent: Dec. 3, 2019

(54) X-RAY CT DEVICE AND BED DEVICE

(71) Applicant: Toshiba Medical Systems Corporation, Otawara-shi (JP)

(72) Inventors: Kiminori Toya, Kawasaki (JP); Tomoki Umetsu, Ota (JP); Keisuke Oishi, Nasushiobara (JP); Masayuki Wakahara, Utsunomiya (JP)

(73) Assignee: Canon Medical Systems Corporation, Otawara-shi (JP)

( * ) Notice: Subject to any disclaimer, the term of this patent is extended or adjusted under 35 U.S.C. 154(b) by 308 days.

(21) Appl. No.: 15/493,558

(22) Filed: Apr. 21, 2017

(65) Prior Publication Data
US 2017/0303873 A1    Oct. 26, 2017

(30) Foreign Application Priority Data

Apr. 25, 2016  (JP) ................................. 2016-087380
Apr. 20, 2017  (JP) ................................. 2017-083833

(51) Int. Cl.
*A61B 6/04*    (2006.01)
*A61B 6/03*    (2006.01)
*A61G 13/02*   (2006.01)
*A61G 13/04*   (2006.01)
*A61G 13/00*   (2006.01)
*A61B 6/00*    (2006.01)

(52) U.S. Cl.
CPC ............ *A61B 6/0407* (2013.01); *A61B 6/035* (2013.01); *A61B 6/4435* (2013.01); *A61G 13/0018* (2013.01); *A61G 13/02* (2013.01); *A61G 13/04* (2013.01)

(58) Field of Classification Search
CPC ..... A61B 6/035; A61B 6/0407; A61B 6/4435; A61G 13/0018; A61G 13/02; A61G 13/04
See application file for complete search history.

(56) References Cited

U.S. PATENT DOCUMENTS

2016/0151024 A1* 6/2016 Goto ..................... A61B 6/027
378/8

FOREIGN PATENT DOCUMENTS

| JP | 2007-159719 | 6/2007 |
| JP | 2010-167189 | 8/2010 |
| JP | 2011-87988  | 5/2011 |

* cited by examiner

*Primary Examiner* — Mark R Gaworecki
(74) *Attorney, Agent, or Firm* — Oblon, McClelland, Maier & Neustadt, L.L.P.

(57) ABSTRACT

An X-ray CT device according to an embodiment includes a gantry, a top board, and a movement mechanism. The gantry includes an X-ray tube that generates X-rays and a detector that detects the X-rays. The top board inserts the subject into the opening section of the gantry. The movement mechanism moves the top board in a longitudinal direction. Furthermore, the position of the top board in a vertical direction at the position that intersects with the path of the X-rays is changed at substantially the same slope relative to the movement distance of the top board when the top board is moved in the longitudinal direction.

12 Claims, 5 Drawing Sheets

X-RAY CT DEVICE AND BED DEVICE

CROSS-REFERENCE TO RELATED APPLICATIONS

This application is based upon and claims the benefit of priority from Japanese Patent Application No. 2016-087380, filed on Apr. 25, 2016; and Japanese Patent Application No. 2017-083833, filed on Apr. 20, 2017, the entire contents of all of which are incorporated herein by reference.

FIELD

Embodiments described herein relate generally to an X-ray computed tomography (CT) device and a bed device.

BACKGROUND

Conventionally, X-ray CT devices include a top board on which the subject is placed, and the top board is moved on the movement path that intersects with the path of X-rays from an X-ray tube to a detector. Furthermore, when capturing is conducted on the subject, the X-ray CT device moves the top board, on which the subject is placed, so that the site to be captured is located at the position that intersects with the path of X-rays.

Here, the top board, included in the X-ray CT device, is generally configured like a cantilever. Therefore, if the top board is moved, residual vibrations, which are vertical vibrations of the subject, may occur immediately after the top board is stopped. In order to improve the image quality of captured images, it is preferable to obtain data with less shaking of the subject, and there is a need to minimize residual vibrations.

DETAILED DESCRIPTION

An X-ray CT device according to an embodiment includes a gantry, a top board, and a movement mechanism. The gantry includes an X-ray tube that generates X-rays and a detector that detects the X-rays. The top board inserts the subject into an opening section of the gantry. The movement mechanism moves the top board in a longitudinal direction. Furthermore, the position of the top board in a vertical direction at the position that intersects with the path of the X-rays is changed at substantially the same slope relative to the movement distance of the top board when the top board is moved in the longitudinal direction.

With reference to the attached drawings, a detailed explanation is given below of an embodiment of an X-ray CT device and a bed device according to the subject application. Furthermore, the embodiment described below is an example, and the X-ray CT device and the bed device according to the subject application are not limited to the following embodiment.

Figure 1:
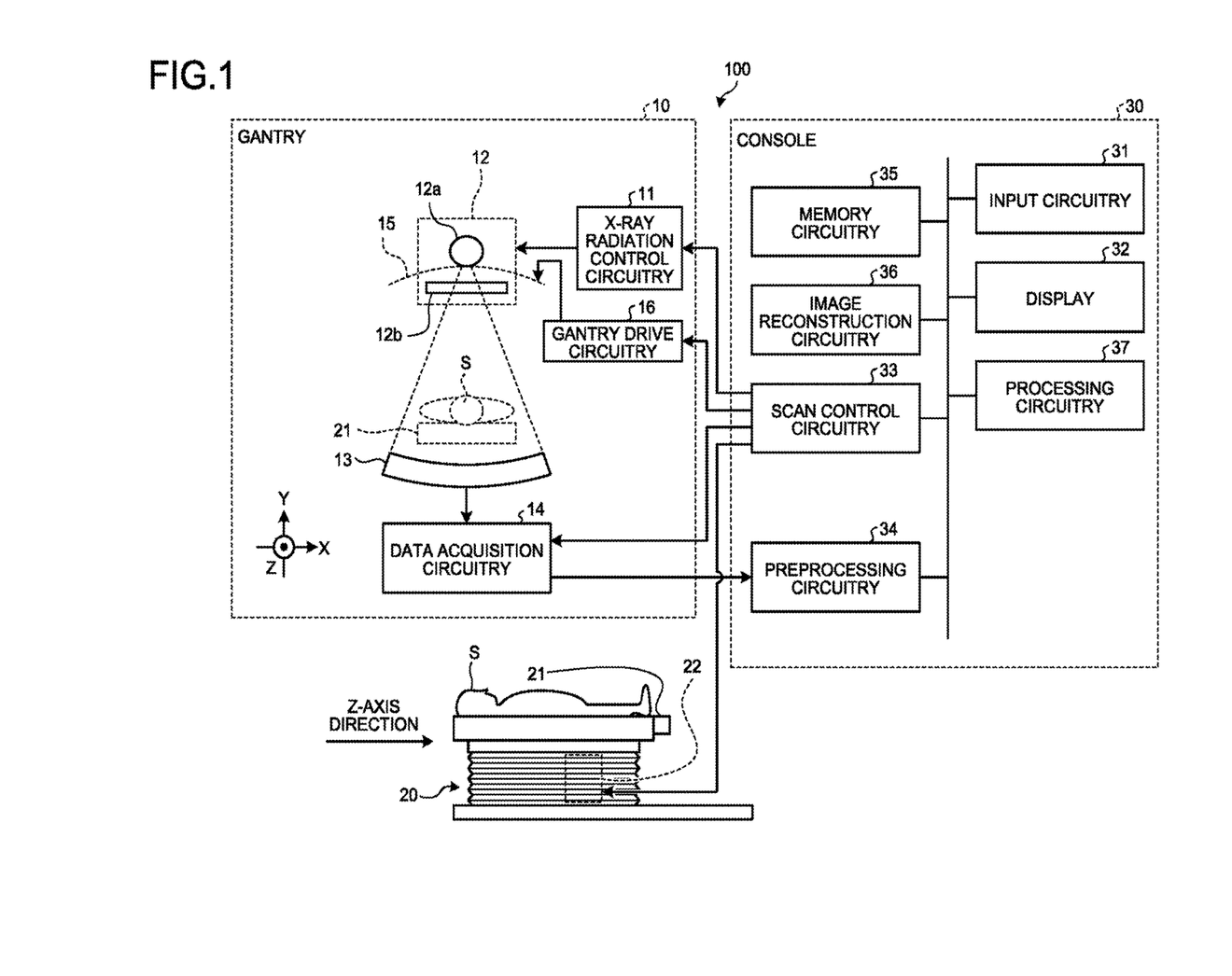
FIG. 1 is a diagram that illustrates an example of the configuration of an X-ray CT device according to the present embodiment.

FIG. 1 is a diagram that illustrates an example of the configuration of the X-ray CT device according to the present embodiment. For example, as illustrated in FIG. 1, an X-ray CT device 100 according to the present embodiment includes a gantry 10, a bed device 20, and a console 30.

Furthermore, according to the present embodiment, in the X-ray CT device 100, the direction in which the gantry 10 and the bed device 20 are arranged parallel is a Z-axis direction, the horizontal direction perpendicular to the Z-axis direction is an X-axis direction, and the vertical direction perpendicular to the Z-axis direction is a Y direction. Furthermore, the direction from the bed device 20 to the gantry 10 along the Z-axis direction is a forward direction, and the direction from the gantry 10 to the bed device 20 is a backward direction. Furthermore, the direction from left to right along the X-axis direction is a right direction, and the direction from right to left is a left direction. Furthermore, the direction from bottom to top along the Y-axis direction is an upward direction, and the direction from top to bottom is a downward direction.

The gantry 10 is a device that emits X-rays to a subject S (patient), detects X-rays, transmitted through the subject S, and outputs them to the console 30. Specifically, the gantry 10 includes an opening section, which is formed in substantially the central part, and emits X-rays to the subject S who is located inside the opening section. For example, the gantry 10 includes X-ray radiation control circuitry 11, an X-ray generation device 12, a detector 13, data acquisition circuitry (DAS: Data Acquisition System) 14, a rotary frame 15, and gantry drive circuitry 16.

The X-ray generation device 12 emits X-rays to the subject S under the control of the X-ray radiation control circuitry 11 that is described later. For example, the X-ray generation device 12 includes an X-ray tube 12a and a collimator 12b. The X-ray tube 12a generates X-rays. Specifically, by using the high voltage that is supplied by an undepicted high-voltage generation device, the X-ray tube 12a generates X-rays that are spread with the fan angle and the cone angle. The collimator 12b narrows the radiation range (the fan angle and the cone angle) of X-rays that are generated by the X-ray tube 12a.

The X-ray radiation control circuitry 11 controls the X-ray generation device 12 under the control of scan control circuitry 33 that is described later. For example, the X-ray radiation control circuitry 11 controls an undepicted high-voltage generation device so as to supply a high voltage to the X-ray tube 12a, included in the X-ray generation device 12. Furthermore, the X-ray radiation control circuitry 11 adjusts the tube voltage or the tube current that is supplied to the X-ray tube 12a, thereby adjusting the amount of X-rays that are emitted to the subject S. Furthermore, the X-ray radiation control circuitry 11 adjusts the numerical aperture of the collimator 12b, included in the X-ray generation device 12, thereby adjusting the radiation range of X-rays.

The detector 13 detects X-rays that are generated by the X-ray tube 12a. For example, the detector 13 is a two-dimensional array type detector (plane detector) that is configured such that multiple detecting element columns are arranged along the Z-axis direction, on which X-ray detecting elements for multiple channels are arranged in the X-axis direction. Furthermore, when capturing of the subject S is conducted, the detector 13 detects X-rays that are transmitted through the subject S.

The rotary frame 15 is a frame that is formed in a circular shape, and it supports the X-ray generation device 12 and the detector 13 such that they are opposed to each other with the opening section, formed in the gantry 10, interposed therebetween. Here, the rotary frame 15 is rotatably provided along the circumference of the opening section that is formed in the gantry 10.

The gantry drive circuitry 16 rotatably drives the rotary frame 15 under the control of the scan control circuitry 33 that is described later. Thus, the gantry drive circuitry 16 rotates the X-ray generation device 12 and the detector 13 in the circular orbit around the subject S as a center, arranged inside the opening section that is formed in the gantry 10.

The data acquisition circuitry 14 acquires projection data from detection data on X-rays that are detected by the detector 13 under the control of the scan control circuitry 33 that is described later. The data acquisition circuitry 14 is also called a Data Acquisition System (DAS). For example, the data acquisition circuitry 14 conducts an amplification process, A/D conversion process, inter-channel sensitivity correction process, or the like, on X-ray intensity distribution data, detected by the detector 13, to generate projection data and transmits the generated projection data to the console 30 that is described later. Furthermore, the inter-channel sensitivity correction process may be conducted by preprocessing circuitry 34 that is described later.

The bed device 20 is the device on which the subject S is placed, and it includes a top board 21, on which the subject S is placed, and a bed driving mechanism 22. The top board 21 is a plate-like member that inserts the subject S into the opening section of the gantry 10. The bed driving mechanism 22 moves the subject S in a vertical direction and in a front-back direction, thereby moving the top board 21 between the X-ray generation device 12 and the detector 13, supported by the rotary frame 15.

The console 30 is a device that receives an operator's operation on the X-ray CT device 100 and that reconstructs CT image data by using the projection data that is acquired by the gantry 10. As illustrated in FIG. 1, the console 30 includes input circuitry 31, a display 32, the scan control circuitry 33, the preprocessing circuitry 34, memory circuitry 35, image reconstruction circuitry 36, and processing circuitry 37.

The input circuitry 31 includes a mouse, keyboard, trackball, switch, button, joystick, or the like, that is used for inputting various commands or various settings by an operator of the X-ray CT device 100, and it transfers commands or information on settings, received from an operator, to the processing circuitry 37. For example, the input circuitry 31 receives, from an operator, the capturing condition of CT image data, the reconstruction condition for reconstructing CT image data, the image processing condition for CT image data, or the like.

The display 32 is a monitor that is viewed by an operator and, under the control of the processing circuitry 37, displays CT images, generated from CT image data, to an operator, and displays a Graphical User Interface (GUI) for receiving various commands, various settings, or the like, from an operator via the input circuitry 31.

The scan control circuitry 33 controls operations of the X-ray radiation control circuitry 11, the gantry drive circuitry 16, the data acquisition circuitry 14, and the bed driving mechanism 22 under the control of the processing circuitry 37, thereby controlling an acquisition process of projection data by the gantry 10. For example, the scan control circuitry 33 conducts helical scan to scan the subject S in a helical fashion by rotating the rotary frame 15 while the top board 21 is moved in a continuous manner.

Furthermore, for example, the scan control circuitry 33 conducts conventional scan to scan the subject S in a circular orbit by rotating the rotary frame 15 with the position of the subject S fixed after the top board 21 is moved. Furthermore, for example, the scan control circuitry 33 implements a step-and-shoot method to conduct conventional scan at multiple capturing positions by moving the position of the top board 21 at a constant interval.

The preprocessing circuitry 34 conducts a logarithmic conversion process and a correction process, such as offset correction, sensitivity correction, or beam hardening correction, on the projection data that is generated by the data acquisition circuitry 14, thereby generating corrected projection data. Then, the preprocessing circuitry 34 stores the generated corrected projection data in the memory circuitry 35.

The memory circuitry 35 stores the projection data that is generated by the preprocessing circuitry 34. Furthermore, the memory circuitry 35 stores CT images, or the like, which are generated by the image reconstruction circuitry 36 that is described later. Moreover, the memory circuitry 35 stores processing results by the processing circuitry 37, which is described later, as appropriate.

The image reconstruction circuitry 36 uses the projection data, stored in the memory circuitry 35, to reconstruct CT image data. Furthermore, the image reconstruction circuitry 36 performs various types of image processing on CT image data, thereby generating various CT images. Furthermore, the image reconstruction circuitry 36 stores, in the memory circuitry 35, reconstructed CT image data and CT images generated during various types of image processing.

The processing circuitry 37 controls operations of the gantry 10, the bed device 20, and the console 30, thereby performing the overall control on the X-ray CT device 100. Specifically, the processing circuitry 37 controls the scan control circuitry 33 so as to control CT scan that is conducted by the gantry 10. Furthermore, the processing circuitry 37 controls the image reconstruction circuitry 36 so as to control an image reconstruction process or an image generation process by the console 30. Furthermore, the processing circuitry 37 controls the display 32 so as to display various types of CT images, stored in the memory circuitry 35.

For example, the processing circuitry 37 is implemented by using a processor. Here, the processor means, for example, a central processing unit (CPU), Graphics Processing Unit (GPU), Application Specific Integrated Circuit (ASIC), programmable logic device (e.g., Simple Programmable Logic Device: SPLD, Complex Programmable Logic Device: CPLD, Field Programmable Gate Array: FPGA), or the like. The processor reads and executes the program stored in the memory circuitry 35, thereby implementing the above-described function. Furthermore, a configuration may be such that, instead of storing a program in the gantry drive circuitry, a program is directly installed in a circuit of the processor. In this case, the processor reads and executes the program, installed in the circuit, to perform a function. Furthermore, with regard to each processor according to the present embodiment, each processor is not necessarily configured as a single circuit, but multiple independent circuits may be combined to be configured as a single processor to perform the function.

Figure 2:
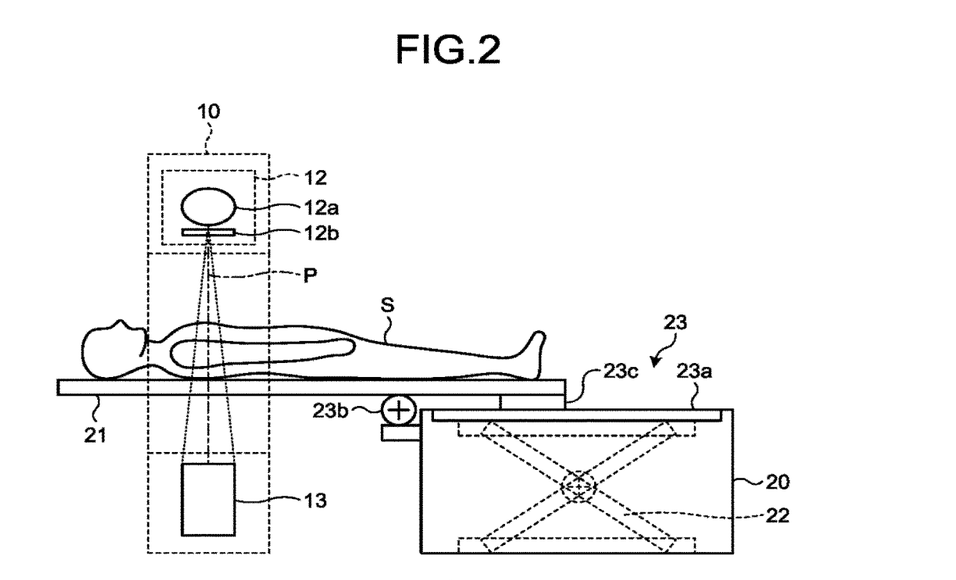
FIG. 2 is a diagram that illustrates an example of the configuration of a bed device according to the present embodiment.

FIG. 2 is a diagram that illustrates an example of the configuration of the bed device 20 according to the present embodiment. For example, as illustrated in FIG. 2, the bed device 20 includes the top board 21, the bed driving mechanism 22, and a movement mechanism 23. Here, for example, the movement mechanism 23 includes a slider 23a, a support section 23b, and a fixed section 23c, and it moves the top board 21 in a longitudinal direction.

The top board 21 has the subject S placed thereon, and it is moved on the movement path that intersects with a path P of X-rays. Specifically, the trailing edge of the top board 21 is fixed to the fixed section 23c on the slider 23a, and the lower surface thereof is supported by the support section 23b. Furthermore, the top board 21 is configured like a cantilever that is projected toward the gantry 10 from the bed device 20 due to driving of the slider 23a such that the entire body of the subject S can be captured.

The bed driving mechanism 22 moves the top board 21 in a front-back direction and in a right-and-left direction to locate the subject S between the X-ray generation device 12 and the detector 13.

The slider 23a movably supports the fixed section 23c along the moving direction of the top board 21. Specifically, the slider 23a is provided in the upper section of the bed driving mechanism 22, and it serves as the trajectory along which the top board 21 is moved.

The support section 23b is in contact with the lower surface of the top board 21 to support the top board 21. Specifically, the support section 23b is provided in front of the upper section of the bed driving mechanism 22, and it has an effect to prevent concentration of stress to the fixed section 23c while the top board 21 is projected. For example, the support section 23b is a roller.

The fixed section 23c is fixed to one end of the top board 21 with respect to the moving direction. Specifically, the fixed section 23c is a movable body that moves on the slider 23a, and it connects to the trailing edge section of the top board 21 so that the top board 21 can move back and forth in the front-back direction.

With the above-described configuration, when capturing is conducted on the subject S, the bed device 20 drives the bed driving mechanism 22 to move the top board 21 on which the subject S is placed, and it stops moving the top board 21 when the site to be captured, e.g., a diseased site, is located at the position that intersects with the path P of X-rays. The position of the top board 21 when the site to be captured is located at the position that intersects with the path P of X-rays, as described above, is referred to as the capturing position.

Here, if the top board 21 is structured like a cantilever as described above, the top board 21 is bent as it protrudes and, as a result, the position of the subject S may be shifted in the direction of gravitational force.

Therefore, the bed device 20 is configured such that, as the top board 21 is projected, the front end of the top board 21 is lifted up so that the positional deviation of the subject S may be reduced.

Figure 3:
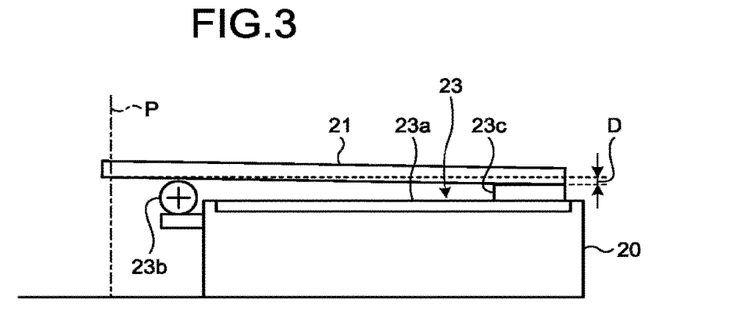
FIG. 3 is a diagram that illustrates an operation of each unit in the bed device according to the present embodiment.
Figure 4:
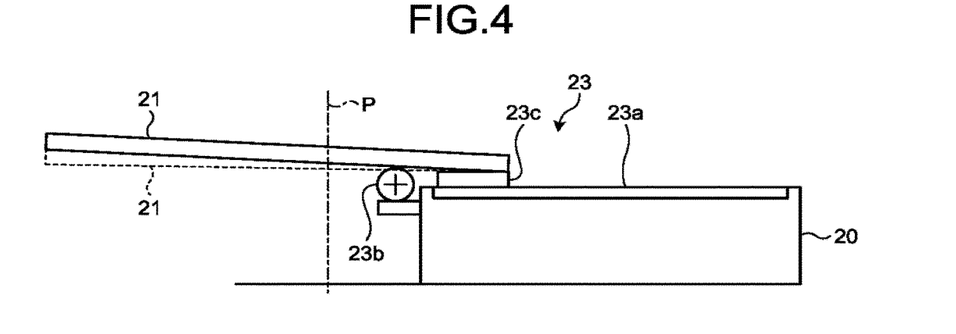
FIG. 4 is a diagram that illustrates an operation of each unit in the bed device according to the present embodiment.

FIGS. 3 and 4 are diagrams that illustrate an operation of each unit in the bed device 20 according to the present embodiment. Here, FIG. 3 illustrates a state where the top board 21 is retracted toward the bed device 20 to a maximum extent, and FIG. 4 illustrates a state where the top board 21 is projected toward the gantry 10 to a maximum extent.

Furthermore, the position of the top board 21 when the top board 21 is retracted toward the bed device 20 to a maximum extent, as illustrated in FIG. 3, is hereafter referred to as the minimum projection position. Moreover, the position of the top board 21 when the top board 21 is projected toward the gantry 10 to a maximum extent, as illustrated in FIG. 4, is referred to as the maximum projection position.

For example, as illustrated in FIGS. 3 and 4, according to the present embodiment, the support section 23b and the fixed section 23c are installed such that a distance D is provided between the support point of the support section 23b and the top surface of the fixed section 23c. With this configuration, as the fixed section 23c comes closer to the support section 23b, the top board 21 is tilted due to a geometric effect of the distance D, and the front end of the top board 21 is lifted up.

Figure 5:
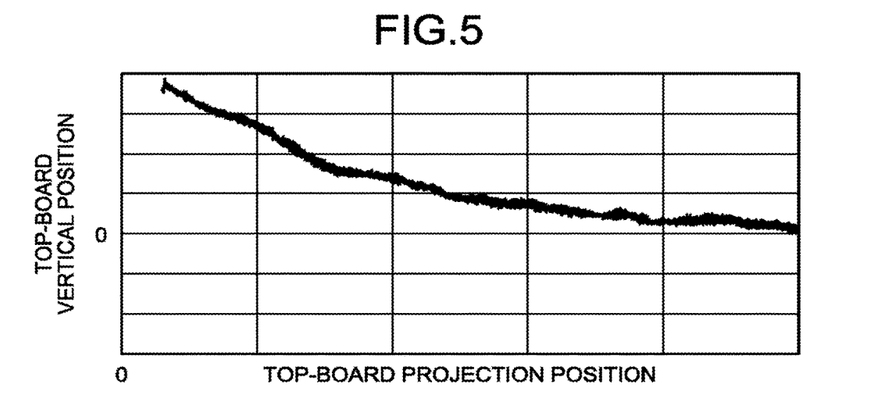
FIG. 5 is a diagram that illustrates an example of the relationship between the top-board projection position and the top-board vertical position when a top board according to the present embodiment is moved in a state where the subject is not placed.

FIG. 5 is a diagram that illustrates an example of the relationship between the top-board projection position and the top-board vertical position when the top board 21 according to the present embodiment is moved in a state where the subject S is not placed. Here, the top-board projection position, represented by the horizontal axis in FIG. 5, indicates the position of the top board 21 when the top board 21 is moved between the maximum projection position and the minimum projection position, and the position when the top board 21 is located in the maximum projection position is zero. Furthermore, the top-board vertical position, represented by the vertical axis in FIG. 5, indicates the position in a vertical direction at the position where the top board 21 intersects with the path P of X-rays, and the position when the top board 21 is in the minimum projection position is zero.

For example, as illustrated in FIG. 5, if the top board 21 is moved in a state where the subject S is not placed, as the top board 21 is projected, the position where the top board 21 intersects with the path P of X-rays becomes higher due to the effect of the support section 23b. With this configuration, if the subject S is placed on the top board 21, the positional deviation of the subject S due to movement of the top board 21 is reduced.

Furthermore, if the top board 21 is structured like a cantilever as described above, when the top board 21 is moved, residual vibrations, i.e., vertical vibrations of the subject S, may occur immediately after the top board 21 is stopped. To improve the image quality of captured images, it is preferable to obtain data with little shaking of the subject S, and there is a need to minimize residual vibrations.

Thus, the X-ray CT device 100 according to the present embodiment is further configured to be able to prevent residual vibrations of the subject S that occurs due to the movement of the top board 21.

Specifically, according to the present embodiment, in the bed device 20, the top board 21 is configured such that the position of the top board 21 in a vertical direction at the position that intersects with the path of X-rays is changed at substantially the same slope relative to the movement distance of the top board 21 during a movement in a longitudinal direction.

For example, the top board 21 is configured such that its lower surface has a projected section that is projected toward the support section 23b so that the surface, being in contact with the support section 23b, is curved in a longitudinal direction.

Figure 6:
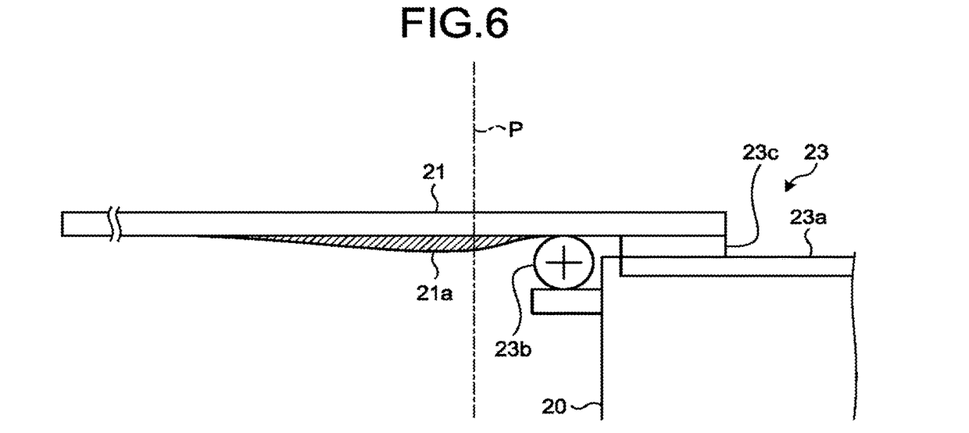
FIG. 6 is a diagram that illustrates an example of a projected section that is included in the top board according to the present embodiment.

FIG. 6 is a diagram that illustrates an example of a projected section 21a that is included in the top board 21 according to the present embodiment. For example, as illustrated in FIG. 6, according to the present embodiment, with regard to the top board 21, the lower surface of the top board 21 has the projected section 21a that is projected toward the support section 23b from the plane that connects both ends of the top board 21 with respect to the moving direction.

Figure 7:
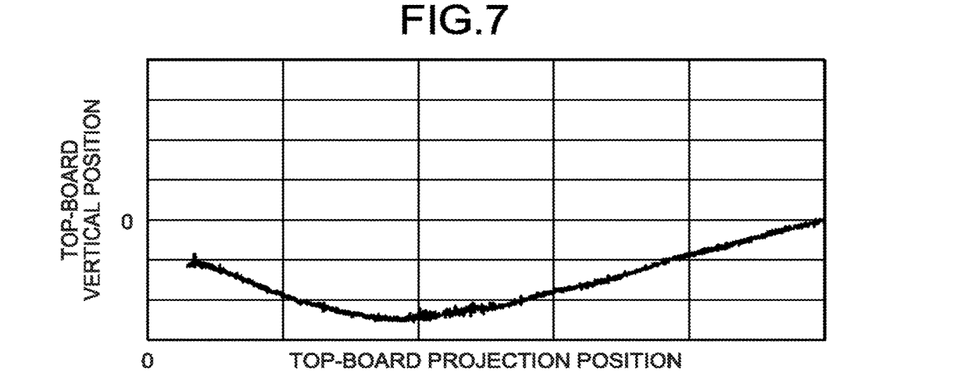
FIG. 7 is a diagram that illustrates an example of the relationship between the top-board projection position and the top-board vertical position in a case where the top board, which is not provided with the projected section according to the present embodiment, is moved in a state where the subject is placed.

According to the present embodiment, the projected section 21a has a function to change the height by which the support section 23b lifts up the top board 21 in accordance with the position of the top board 21, and it functions so as to eliminate changes in the slope of the curved line that represents the relationship between the top-board projection position and the top-board vertical position, as illustrated in FIG. 7. Thus, the projected section 21a has effects to reduce the acceleration that occurs on the top board 21 in a vertical direction and to reduce residual vibrations.

A detailed explanation is given below of the projected section 21a according to the present embodiment. Furthermore, in order to clarify the configuration and the function of the projected section 21a, an explanation is first given below of an example of the case where the projected section 21a is not provided on the top board 21 and then an explanation is given of an example of the case where the projected section 21a is provided on the top board 21.

FIG. 7 is a diagram that illustrates an example of the relationship between the top-board projection position and the top-board vertical position in a case where the top board 21, which is not provided with the projected section 21a according to the present embodiment, is moved in a state where the subject S is placed. Here, the top-board projection position, indicated by the horizontal axis in FIG. 7, represents the same position as the top-board projection position indicated by the horizontal axis in FIG. 5. Furthermore, the top-board vertical position, indicated by the vertical axis in FIG. 7, represents the same position as the top-board vertical position indicated by the vertical axis in FIG. 5.

For example, as illustrated in FIG. 7, in a case where the top board 21 is not provided with the projected section 21a, if the top board 21 is moved in a state where the subject S is placed, as the top board 21 is projected, the position where the top board 21 intersects with the path P of X-rays is gradually lowered and, after passing through a specific position, it is gradually raised. Here, it is considered that the position where the top board 21 intersects with the path P of X-rays is lowered because of bending of the top board 21 due to gravity. Furthermore, it is considered that the position where the top board 21 intersects with the path P of X-rays is raised after passing through a specific position because of the effect of the support section 23b.

Figure 8:
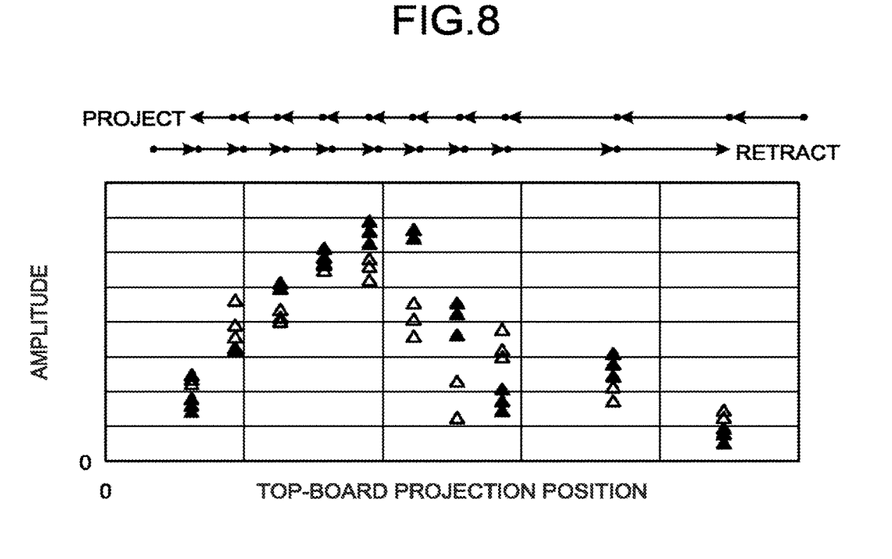
FIG. 8 is a diagram that illustrates an example of the residual vibrations that occur if the top board, which is not provided with the projected section according to the present embodiment, is moved in a state where the subject is placed.

FIG. 8 is a diagram that illustrates an example of the residual vibrations that occur if the top board 21, which is not provided with the projected section 21a according to the present embodiment, is moved in a state where the subject S is placed. Here, the top-board projection position, indicated by the horizontal axis in FIG. 8, represents the same position as the top-board projection position indicated by the horizontal axis in FIG. 7. Furthermore, the amplitude, indicated by the vertical axis in FIG. 8, represents the amplitude of the residual vibration that occurs in the position where the top board 21 intersects with the path P of X-rays. Furthermore, in FIG. 8, white triangles represent the amplitude of the residual vibration at each position in a case where the top board 21 is moved in a direction to which it is projected toward the gantry 10 and it is stopped at multiple different positions. Furthermore, in FIG. 8, black triangles represent the amplitude of the residual vibration at each position in a case where the top board 21 is moved in a direction to which it is retracted toward the bed device 20 and it is stopped at multiple different positions.

For example, as illustrated in FIG. 8, the amplitude of the residual vibration, which occurs at the position where the top board 21 intersects with the path P of X-rays, is different in accordance with the position where the top board 21 is stopped. Here, as it is considered that the frequency of the residual vibration is about several Hz and the rotation frequency of the rotary frame 15 is several Hz at most, it can be said that shaking of the subject S is more likely to occur at the position where the amplitude is higher.

Furthermore, the position where the amplitude is high, illustrated in FIG. 8, matches the position where the slope of the curved line is changed as illustrated in FIG. 7. It can be said that changes of the slope of the curved line, illustrated in FIG. 7, mean that the acceleration occurs in a vertical direction and the position where the slope changes is the position where the vertical forces occur on the top board 21. If the top board 21 is being moved and the movement of the top board 21 is stopped immediately after the force occurs, the top board 21, which is bent in a vertical direction due to the force, starts to have residual vibrations due to the resonance frequency at the stopped position.

The occurrence of residual vibrations on the top board 21 by the above mechanism can be a cause of a decrease in the image quality of tomographic images due to shaking of the subject S. Furthermore, if there is a stand-by for capturing until vibrations are eliminated, it may cause a decrease in the capturing throughput, or the like. Furthermore, if the amplitude of residual vibration is different at each position of the top board 21, it may cause a change in the image quality in accordance with a position on the top board 21. Moreover, if the position on the top board 21 where residual vibrations are large is not used for capturing, it may cause a decrease in flexibility of the position where the subject S is placed, or the like.

Contrary to the above, according to the present embodiment, the lower surface of the top board 21 has the projected section 21a that is projected toward the support section 23b from the plane that connects both ends of the top board 21 with respect to the moving direction.

For example, as illustrated in FIG. 6, the projected section 21a is locally provided on at least part of the lower surface of the top board 21. For example, as illustrated in FIG. 7, if the top board 21 is not provided with the projected section 21*a*, as the top board 21 is projected, the position where the top board 21 intersects with the path P of X-rays is gradually lowered and, after passing through a specific position, it is gradually raised. That is, the amount of displacement of the top board 21 in a vertical direction is locally large at a specific position. Therefore, the projected section 21*a* is locally provided on the position of the lower surface of the top board 21, where the amount of displacement in a vertical direction is locally large, whereby the amount of displacement of the top board 21 in a vertical direction may be reduced while the top board 21 is moved along the movement path. Thus, it is possible to reduce residual vibrations of the subject S, which occurs due to the movement of the top board.

More specifically, as illustrated in FIG. 6, for example, the projected section 21*a* is provided at the position closer to the center of the top board 21 than both ends of the top board 21 with respect to a moving direction. For example, as illustrated in FIG. 7, if the top board 21 is not provided with the projected section 21*a*, as the top board 21 is projected, the position where the top board 21 intersects with the path P of X-rays is gradually lowered and it is gradually raised from the middle. Specifically, the amount of displacement of the top board 21 in a vertical direction is larger at the position closer to the center than at the positions of both ends of the top board 21 with respect to the moving direction. Therefore, the projected section 21*a* is provided on the position closer to the center of the top board 21 than both ends of the top board 21 with respect to the moving direction, whereby it is possible to reduce the amount of displacement of the top board 21 in a vertical direction when the top board 21 is moved along the movement path. Thus, it is possible to reduce residual vibrations of the subject S, which occurs due to the movement of the top board 21.

Furthermore, although FIG. 6 illustrates the case where the single projected section 21*a* is provided on the lower surface of the top board 21, the embodiment is not limited to this, and the multiple projected sections 21*a* may be provided on the lower surface of the top board 21.

More specifically, for example, the projected section 21*a* is formed into a shape such that the thickness in the vertical direction is changed along the moving direction of the top board 21 so that the amount of displacement of the top board 21 in the vertical direction at the position that intersects with the path P of X-rays is changed at substantially the same slope relative to the movement distance of the top board 21 along the movement path. Furthermore, the amount of displacement of the top board 21 in the vertical direction, mentioned here, may be the value that is obtained by the actual measurement, or it may be the value that is obtained by simulation.

Figure 9:
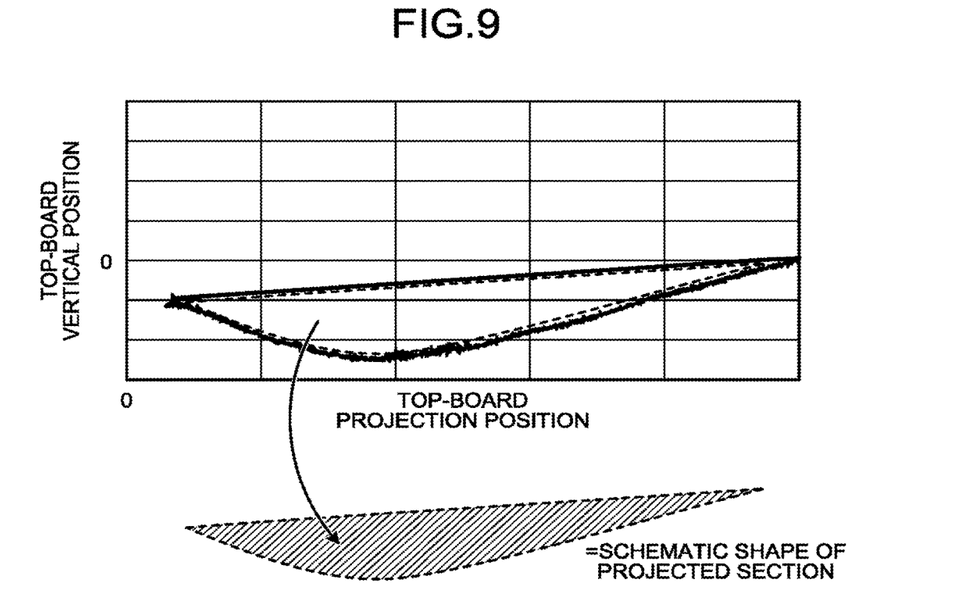
FIG. 9 is a diagram that illustrates an example of the relationship between the top-board projection position and the top-board vertical position in a case where the top board, which is provided with the projected section according to the present embodiment, is moved in a state where the subject is placed.

FIG. 9 is a diagram that illustrates an example of the relationship between the top-board projection position and the top-board vertical position in a case where the top board 21, which is provided with the projected section 21*a* according to the present embodiment, is moved in a state where the subject S is placed. Here, the top-board projection position, indicated by the horizontal axis in FIG. 9, represents the same position as the top-board projection position indicated by the horizontal axis in FIG. 7. Furthermore, the top-board vertical position, indicated by the vertical axis in FIG. 9, represents the same position as the top-board vertical position indicated by the vertical axis in FIG. 7. Furthermore, in FIG. 9, the change indicated by the curved line represents the change in the amount of displacement in a vertical direction relative to the movement distance along the movement path of the top board 21 in a case where the top board 21 is not provided with the projected section 21*a*, as illustrated in FIG. 7.

Here, as illustrated in FIGS. 7 and 8, it is understood that the amplitude of residual vibrations is small in such the range that the slope of the curved line, which represents changes in the top-board vertical position if the top board 21 is not provided with the projected section 21*a*, is substantially the same. This indicates that, if the position of the top board 21 in a vertical direction is linearly changed, the moving speed of the top board 21 in a vertical direction is the same, and the occurrence of acceleration is reduced immediately after the movement of the top board 21 is stopped.

Therefore, as illustrated in FIG. 9, for example, if the shape of the projected section 21*a* is designed such that the amount of displacement in the vertical direction relative to the movement distance of the top board 21 along the movement path linearly changes over the entire range within which the top board 21 is moved, it is considered that the amplitude of residual vibrations over the entire range is reduced. That is, the shape of the cross-sectional surface of the projected section 21*a* along the moving direction of the top board 21 is designed so as to have the shape that is surrounded by the straight line and the curved line, illustrated in FIG. 9.

Here, for example, the amount of displacement of the top board 21 in a vertical direction is changed due to the mass of the subject, or the design of the top board, the support section, or the slider. Therefore, for example, design of the shape of the projected section 21*a* is conducted on the basis of the relationship between the position of the top board 21 and the vertical movement, which is obtained as a numerical value during an experiment that uses a known technology, such as distance measurement, which obtains the data illustrated in FIG. 7, or a known numerical analysis technology, such as 3D Finite Element Method (FEM) analysis.

Furthermore, if the mass of the subject S, placed on the top board 21, is low, residual vibrations are eliminated in a short time due to damping forces, such as viscous elasticity of the entire bed device 20. Therefore, residual vibrations become a problem when the maximum mass as the subject S is placed on the top board 21. Therefore, for example, the shape of the projected section 21*a* is designed such that the movement of the top board 21 is linear if the maximum mass is placed, as determined on the basis of safety, or the like, of the X-ray CT device 100, whereby significant effects may be achieved.

For example, if the data, illustrated in FIG. 7, is acquired by using the top board 21 that is not provided with the projected section 21*a*, the required shape of the projected section 21*a* may be experimentally obtained as illustrated in FIG. 9. For example, if the lower surface of the top board 21 is projected like the shape that is illustrated in the lower section of FIG. 9, it is expected that the top board 21 moves linearly.

More specifically, as the rotation center is the trailing edge section of the top board 21, the lifting height of the top board 21 at the position where the top board 21 intersects with the path P of X-rays is more than the lifting height at the position of the support section 23*b*. Therefore, the amount of lifting of the top board 21, required at the position of the support section 23*b*, needs to be obtained by numerical analysis. Furthermore, it is necessary to make a design for the entire movable range of the top board 21.

Furthermore, it is preferable that the shape of the projected section 21*a* is designed such that the vertical movement of the position of the center of gravity of the top board 21 is linear in a state where the subject S is placed. This is because forces occur on the top board 21 due to movement of the center of gravity of the top board 21. By making such a design, vibrations of the top board 21 at the position where the top board 21 intersects with the path P of X-rays may be reduced more effectively.

For example, the projected section 21a may be formed by gluing a member, serving as the projected section 21a, to the existing top board 21. In this case, for example, the projected section 21a is formed by gluing a component that is shaped by cutting, a 3D printer, or the like.

As described above, according to the present embodiment, the projected section 21a changes the height by which the support section 23b lifts the top board 21 up in accordance with the position of the top board 21 so that the acceleration that occurs on the top board 21 in a vertical direction is reduced. Therefore, according to the present embodiment, it is possible to reduce residual vibrations of the subject S, which occurs due to the movement of the top board 21.

Furthermore, in the above-described embodiment, an explanation is given of an example of the case where the projected section 21a is formed as a component separate from the top board 21 and it is glued to the top board 21; however, the embodiment is not limited to this. For example, the projected section may be integrally formed with the top board. In this case, for example, the projected section is formed by cutting the lower surface of the top board.

Figure 10:
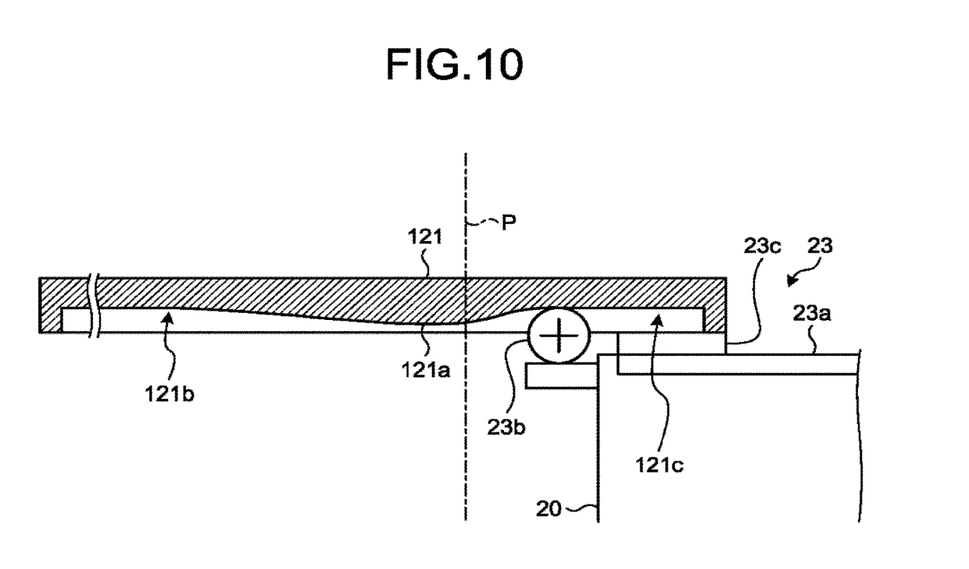
FIG. 10 is a diagram that illustrates an example of the case where the projected section according to the present embodiment is integrally formed with the top board.

FIG. 10 is a diagram that illustrates an example of the case where the projected section according to the present embodiment is integrally formed with the top board. For example, as illustrated in FIG. 10, a recessed section 121b is formed by cutting the lower surface of a top board 121 at the front end side and a recessed section 121c is formed by cutting the lower surface at the trailing edge side so that a projected section 121a is formed, which is projected toward the support section 23b from the plane that connects the two recessed sections 121b and 121c.

Furthermore, if the projected section 121a is integrally formed with the top board 121 as described above, for example, the projected section 121a is locally provided on at least part of the lower surface of the top board 121. Furthermore, for example, the projected section 121a is provided on the position closer to the center of the top board 121 than both ends of the top board 121 with respect to the moving direction. Furthermore, the projected section 121a may be provided on part of the lower surface of the top board 121 or may be provided on multiple areas.

Furthermore, if the projected section 121a is integrally formed with the top board 121 as described above, a cuttable material with high X-ray transmissivity is used for the top board 121. For example, such a material is preferably a resin, such as epoxy. Furthermore, in a case where a fibrous reinforcing material, such as Carbon Fiber Reinforced Plastic (CFRP), is used as the material of the top board 121, if the part to be cut has fibers, it may be difficult to produce a smooth curved line by cutting. Therefore, if a fibrous reinforcing material is used as the material of the top board 121, it is preferable that a thick resin layer is previously formed by using a fiber-impregnating resin, or the like, on the part to be cut before the top board 121 is formed. The top board 121 needs strength as compression stress is applied to the lower surface of the top board 121 when it is bent; the stress is largest at the trailing edge section. As illustrated in FIG. 9, the projected section 121a is provided on the position apart from the trailing edge section of the top board 121; therefore, it is considered that the top board 121 is unlikely to be damaged due to compression stress. Furthermore, processing of the projected section 121a may be achieved by using a known NC processor, a finishing technology, or the like.

Furthermore, in the above-described embodiment, an explanation is given of an example of the case where the distance D is provided between the support point of the support section 23b and the top surface of the fixed section 23c; however, the embodiment is not limited to this. For example, even if a configuration is such that the support point of the support section and the top surface of the fixed section are on the same level, the projected section is provided on the lower surface of the top board so that residual vibrations of the subject, which occur due to movement of the top board, may be reduced.

Here, as described above, if the top board 21 is configured like a cantilever, the top board 21 is bent as it is projected, and accordingly the position of the subject S may be shifted in the direction of gravitational force.

Therefore, if a configuration is such that the support point of the support section and the top surface of the fixed section are on the same level, the projected section is formed into a shape in consideration of the above-described bending of the top board. Specifically, in this case, the projected section is formed into such a shape that the thickness in a vertical direction is changed along the moving direction of the top board so that the amount of displacement in a vertical direction, including the amount of displacement due to bending of the top board at the position that intersects with the path of X-rays, is changed at substantially the same slope relative to the movement distance along the movement path of the top board.

Furthermore, in the above-described embodiment, an explanation is given of an example of the case where, in the bed device 20, the top board is configured such that the position of the top board in a vertical direction at the position that intersects with the path of X-rays is changed at substantially the same slope relative to the movement distance of the top board during a movement in a longitudinal direction; however, the embodiment is not limited to this. For example, in the bed device 20, the movement mechanism 23 may be configured such that the position of the top board in a vertical direction at the position that intersects with the path of X-rays is changed at substantially the same slope relative to the movement distance of the top board during a movement in the longitudinal direction.

Figure 11:
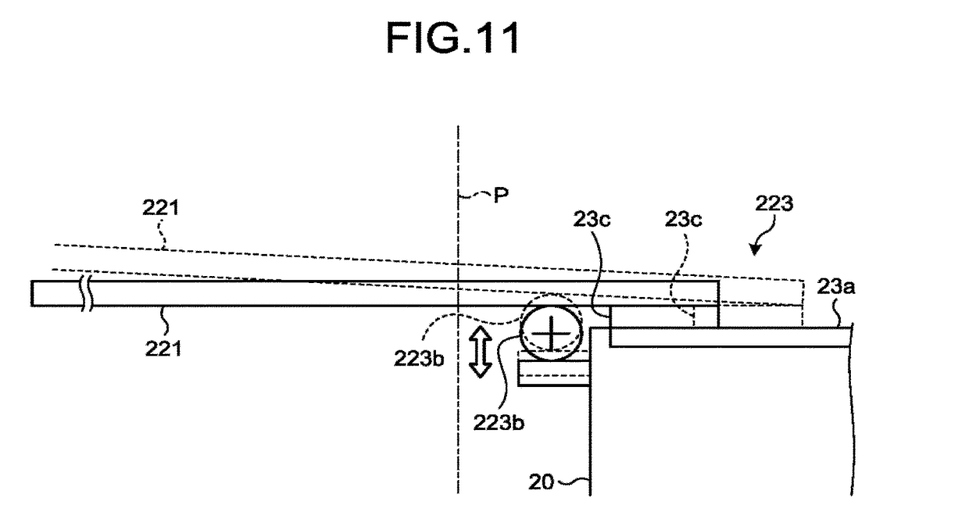
FIG. 11 is a diagram that illustrates an example of a movement mechanism according to a modified example of the present embodiment.

FIG. 11 is a diagram that illustrates an example of a movement mechanism 223 according to a modified example of the present embodiment. For example, as illustrated in FIG. 11, a support section 223b, included in the movement mechanism 223, moves the top board 221 in a vertical direction such that the position of the top board 221 in a vertical direction at the position that intersects with the path of X-rays is changed at substantially the same slope relative to the movement distance of the top board in accordance with the movement of the top board 221 in the longitudinal direction. For example, the support section 223b is moved in a vertical direction by a movement mechanism, or the like, that is provided in the bed device 20 so that it moves the top board 221 in a vertical direction. Furthermore, in this modified example, the top board 221 may or may not include a projected section that is explained in the above-described embodiment.

In this case, for example, the processing circuitry 37 controls operations of the support section 223b. For example, the processing circuitry 37 derives the curved line (e.g., the curved line that is illustrated in FIG. 7), which indicates the relationship between the top-board projection position and the top-board vertical position if the top board 221 is moved in a state where the subject is placed, on the basis of the attribute of the subject or the capturing condition by simulation. Furthermore, the attribute of the subject here means, for example, the body height or the body weight. Furthermore, the capturing condition is, for example, the site to be captured, or the direction of the subject when the subject is inserted into the opening section of the gantry 10 (Head First (HF): the subject is inserted from the head side, Foot First (FF): the subject is inserted from the foot side, or the like).

Here, for example, the processing circuitry 37 may derive the curved line that indicates the relationship between the top-board projection position and the top-board vertical position by calculation or may derive it by using the actual measurement data that actually measures the top-board vertical position while the top-board projection position is changed. Here, for example, with regard to the actual measurement data, individual data is previously stored in the memory circuitry 35 for each attribute of the subject or each capturing condition, and it is appropriately read to be used by the processing circuitry 37. Alternatively, for example, with regard to the actual measurement data, the data, actually measured under the standard condition, may be previously stored in the memory circuitry 35 and may be appropriately corrected for use by the processing circuitry 37 in accordance with the attribute of the subject or the capturing condition.

Afterward, the processing circuitry 37 calculates the movement distance of the top board 221 in a vertical direction at each position along the moving direction of the top board 221 on the basis of the curved line that is derived by simulation. Here, the processing circuitry 37 calculates the movement distance in a vertical direction at each position of the top board 221 so as to correct the curved line, derived by simulation, to be a straight line over the entire range within which the top board 221 is moved. Then, when the top board 221 is moved in a longitudinal direction, the processing circuitry 37 moves the support section 223b vertically by the calculated movement distance at each position of the top board 221 with respect to the moving direction, thereby moving the top board 221 in a vertical direction.

Thus, the amount of displacement in a vertical direction relative to the movement distance of the top board 221 along the movement path is linearly changed over the entire range within which the top board 221 is moved. As a result, the moving speed of the top board 221 in a vertical direction is the same, and the occurrence of acceleration is reduced immediately after movement of the top board 221 is stopped. Therefore, according to this modified example, it is possible to reduce residual vibrations of the subject, which occur due to the movement of the top board.

According to at least one of the above-described embodiments, it is possible to reduce residual vibrations of the subject, which occur due to movement of the top board.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT device, comprising:
   a gantry including an X-ray tube configured to generate an X-ray, and a detector configured to detect the X-ray;
   a top board configured to insert a subject into an opening section of the gantry; and
   a movement mechanism configured to move the top board in a longitudinal direction,
   wherein a position of the top board in a vertical direction at a position that intersects with a path of the X-ray is changed at substantially a same slope relative to a movement distance of the top board when the top board is moved in the longitudinal direction, so that acceleration that occurs on the top board in a vertical direction is reduced.

2. The X-ray CT device according to claim 1, wherein the movement mechanism includes a support section configured to support the top board by being in contact with a lower surface of the top board, and
   a surface of the top board, being in contact with the support section, is curved in the longitudinal direction.

3. The X-ray CT device according to claim 1, wherein the movement mechanism includes
   a support section configured to support the top board by being in contact with a lower surface of the top board;
   a fixed section configured to be fixed to one end of the top board with respect to a moving direction; and
   a slider configured to movably support the fixed section along a moving direction of the top board, and
   the lower surface of the top board includes a projected section configured to be projected toward the support section from a plane that connects both ends of the top board with respect to a moving direction.

4. The X-ray CT device according to claim 3, wherein the projected section is locally provided on at least part of a lower surface of the top board.

5. The X-ray CT device according to claim 4, wherein the projected section is provided on a position closer to a center of the top board than both ends of the top board with respect to a moving direction.

6. The X-ray CT device according to claim 3, wherein the projected section is formed into a shape such that a thickness in a vertical direction is changed along the moving direction so that an amount of displacement of the top board in a vertical direction at a position that intersects with the path of the X-ray is changed at substantially a same slope relative to a movement distance along a movement path of the top board.

7. The X-ray CT device according to claim 6, wherein an amount of displacement of the top board in a vertical direction is a value that is obtained from actual measurement.

8. The X-ray CT device according to claim 6, wherein an amount of displacement of the top board in a vertical direction is a value that is obtained by simulation.

9. The X-ray CT device according to claim 3, wherein the projected section is integrally formed with the top board.

10. The X-ray CT device according to claim 1, wherein the movement mechanism moves the top board in a vertical direction such that the position of the top board in a vertical direction at the position that intersects with the path of X-rays is changed at substantially a same slope relative to the movement distance of the top board in accordance with the movement of the top board in the longitudinal direction.

11. An X-ray CT device, comprising:
a gantry including an X-ray tube configured to generate an X-ray, and a detector configured to detect the X-ray;
a top board configured to insert a subject into an opening section of the gantry; and
a movement mechanism configured to include a support section, supporting the top board by being in contact with a lower surface of the top board, and move the top board in a longitudinal direction,
wherein a surface of the top board, being in contact with the support section, is curved in the longitudinal direction so that acceleration that occurs on the top board in a vertical direction is reduced.

12. A bed device, comprising:
a top board on which a subject is placed; and
a movement mechanism configured to include a support section, supporting the top board by being in contact with a lower surface of the top board, and to move the top board in a longitudinal direction,
wherein a surface of the top board, being in contact with the support section, is curved in the longitudinal direction so that acceleration that occurs on the top board in a vertical direction is reduced.

* * * * *